(12) United States Patent
Patois et al.

(10) Patent No.: US 6,232,490 B1
(45) Date of Patent: May 15, 2001

(54) METHOD FOR PREPARING ACETIC ACID AND/OR METHYL ACETATE BY METHYL FORMATE ISOMERIZATION

(75) Inventors: Carl Patois, Lyons; Robert Perron, Charly; Daniel Thiebaut, Billere, all of (FR)

(73) Assignee: Acetex Chimie, Paris (FR)

( * ) Notice: Subject to any disclaimer, the term of this patent is extended or adjusted under 35 U.S.C. 154(b) by 0 days.

(21) Appl. No.: 09/142,176
(22) PCT Filed: Mar. 27, 1997
(86) PCT No.: PCT/FR97/00553
 § 371 Date: Sep. 23, 1998
 § 102(e) Date: Sep. 23, 1998
(87) PCT Pub. No.: WO97/35829
 PCT Pub. Date: Oct. 2, 1997

(30) Foreign Application Priority Data

Mar. 27, 1996 (FR) .................................................. 96 03781

(51) Int. Cl.$^7$ ............................ C07C 51/16; C07C 69/02
(52) U.S. Cl. ............................................. 560/231; 562/523
(58) Field of Search ..................... 560/232, 231; 562/517, 518, 519, 523, 607

(56) References Cited

U.S. PATENT DOCUMENTS

| | | | |
|---|---|---|---|
| 4,613,693 | * | 9/1986 | Ray . |
| 5,723,660 | * | 3/1998 | Morimoto et al. . |
| 5,847,204 | * | 12/1998 | Nobel . |
| 5,883,295 | * | 3/1999 | Sunley et al. . |

\* cited by examiner

*Primary Examiner*—Gary Geist
*Assistant Examiner*—Robert W. Deemie
(74) *Attorney, Agent, or Firm*—Dennison, Scheiner, Schultz & Wakeman

(57) ABSTRACT

A method for the preparation of acetic acid and/or methyl acetate by isomerization of methyl formate in a reaction mixture which includes water, a solvent and a catalytic system containing a halogenated promoter and an iridium-based compound. Carbon monoxide is present in the reaction mixture at a partial pressure between $0.1.10^5$ Pa and $25.10^5$ Pa, methyl formate is maintained below 20% by weight of the reaction mixture and water is maintained in an amount which is at most 5% by weight of the reaction mixture. In a typical system, method formate isomerizes to acetic acid according to the reaction:

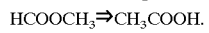

15 Claims, No Drawings

METHOD FOR PREPARING ACETIC ACID AND/OR METHYL ACETATE BY METHYL FORMATE ISOMERIZATION

BACKGROUND OF THE INVENTION

The object of the present invention is the preparation of acetic acid and/or methyl acetate, by using an isomerisation reaction of methyl formate.

Various means of access to acetic acid are known and used industrially. Amongst these are the carbonylation reactions of methanol. This carbonylation reaction may notably be carried out in the liquid phase, under the pressure of carbon monoxide, which is one of the reagents, in the presence of a homogeneous catalytic system comprising a compound based on rhodium and/or iridium and an iodinated promoter.

Another means of access is constituted by the isomerisation reaction of methyl formate in the presence of a catalyst based on rhodium or iridium.

In the isomerisation methods catalysed by iridium, the reaction is carried out with a solvent which is selected from the carboxylic acids, and more particularly, the acid produced. The reaction is moreover carried out under an atmosphere comprising nitrogen. It has in fact been noted that the carbon monoxide did not bring about any particular advantage during the reaction and could even be the cause of a certain inhibition of the isomerisation reaction, it favouring side reactions. It is to be noted that such a behaviour is entirely different from that which is observed when the catalytic system is rhodium-based, in which case the presence of carbon monoxide is essential for keeping the metal in the homogeneous phase. This type of method, whose interest is not questioned, does not have any real interest industrially since the reaction which is described therein is not sufficiently efficient. In fact, the reaction rates are only in the order of 2 mol/h/l of acid and/or ester produced.

It has been proposed, in order to improve the results of the above-mentioned method, to use the isomerisation reaction in the presence of a strong acid of the sulphonic acid type, such as paratoluenesulphonic acid for example. Under the conditions of this method, the reaction is carried out using significant amounts of methyl formate to be isomerised, which is consequently also used as solvent for the reaction. If this improvement contributes to the improvement of the activity of the reaction, it does nevertheless have the disadvantage of necessitating the use of a further compound, which does not simplify the method.

Further, it is possible that this acid degrades under the conditions of the reaction medium.

SUMMARY OF THE INVENTION

An aim of the present invention is to propose a method of isomerisation of methyl formate, into acetic acid and/or methyl acetate, whose productivity is improved with respect to the two isomerisation variants described above, this without it being necessary to employ a further compound to this end.

Furthermore, the method according to the invention is very selective.

These and other goals are met by the present invention which has therefore for object the preparation of acetic acid and/or methyl acetate, by reaction of methyl formate, in the presence of water, a solvent and a catalytic system comprising at least one halogenated promoter and at least one iridium-based compound. The reaction according to the present invention is characterised by the fact that it is carried out in maintaining a partial carbon monoxide pressure between $0.1 \cdot 10^5$ Pa and $25 \cdot 10^5$ Pa, and in maintaining a methyl formate amount of below 20% by weight of the reaction mixture.

It has in fact been noted, on the contrary to what was asserted in the prior art, that the presence of carbon monoxide was essential for the isomerisation reaction of the ester in the presence of iridium.

Furthermore, another important characteristic of the reaction is that the amount of methyl formate which reacts must be at the most 20% in order to obtain the best productivities.

Thus, the combination of these two characteristics has enabled multiplying the productivity of the first method described by 10, simply by maintaining the conditions of partial carbon monoxide pressure and ester concentration during the reaction within the intervals mentioned. Furthermore, the productivity of the method according to the invention is better than that of the variant which comprises strong acid since reaction rates of the same, even greater order of magnitude, have been obtained at lower temperatures.

DETAILED DESCRIPTION OF THE INVENTION

For greater clarity, the nature of the reagents shall first of all be described.

Thus, the reaction is carried out with methyl formate.

The method of the invention is carried out in the presence of a catalytic system which comprises at least one halogenated promoter and at least one iridium-based compound.

The halogenated promoter, which represents one of the constituents of the catalytic system, is selected preferably from iodinated compounds.

The halogenated promoter may be in the form of iodine, alone or in combination with other elements such as for example hydrogen, a $C_1$–$C_{10}$ alkyl radical, a $C_1$–$C_{10}$ acyl radical, a $C_6$–$C_{10}$ aryl radical, or even alkali metal iodides or metal iodides, such as transition metal iodides, or iodides of metals of column II A of the periodic classification of the elements.

It is to be noted that the halogenated promoter may be constituted of a mixture of several of the above-mentioned promoters.

The context of the present invention shall not be left in preparing said halogenated promoters in situ with the aid of appropriate precursors.

As examples of promoters which are appropriate to the present invention, iodine, hydroiodic acid, methyl iodide, ethyl iodide, 1,1-diiodoethane, acetyl iodide, aluminium iodide, chromium iodide, lithium iodide, potassium iodide may be notably cited, without intending to be limiting.

According to a particular embodiment of the invention, the promoter used comprises hydrogen or a $C_1$–$C_{10}$ alkyl radical. Preferably, the halogenated promoter comprises iodine and a radical of the methyl type.

The second element of the catalytic system used in the method according to the invention is constituted by at least one iridium-based compound.

First of all, the reaction according to the invention is more particularly carried out in the presence of a homogeneous catalyst. In other words, this signifies that the iridium-based compound is notably in a form which is soluble in the reaction mixture. It is to be noted that the presence of a part of said iridium-based compound in a non-dissolved form, does not have any major difficulty for the implementation of the reaction.

All the iridium compounds which are soluble or able to be dissolved in the reaction medium, under the conditions of implementation of the reaction, may be used. As examples, and without intending to be limiting, metallic iridium, its simple salts, its oxides or even its co-ordination complexes may notably be appropriate in the implementation of the invention.

As simple iridium salts, the iridium halides are conventionally used. The halogen is most particularly selected from chlorine, bromine and iodine, the latter being preferred. Thus, compounds such as $IrI_3$, $IrBr_3$, $IrCl_3$, $IrI_3.4H_2O$, $IrI_4$, $IrBr_3.4H_2O$ may be used in the method according to the invention.

Oxides selected from $IrO_2$, $Ir_2O_3.xH_2O$ may equally be conveniently used in the method according to the invention.

Regarding the soluble co-ordination complexes of iridium, the compounds which are most commonly used are those having ligands selected from carbon monoxide, or a carbon monoxide/halogen combination, the halogen being selected from chlorine, bromine or more particularly iodine. It is not nevertheless excluded to use soluble iridium complexes whose ligands are selected from the organo-phosphorus compounds and organo-nitrogen compounds for example.

As co-ordination complexes known to the person skilled in the art which are particularly convenient in the implementation of the invention, $Ir_4(CO)_{12}$, $Ir(CO)_2I_2{}^-Q^+$, $Ir(CO)_2Br_2{}^-Q^+$, $Ir(CO)_2Cl_2{}^-Q^+$, may be cited without intention to limit; in which formulae Q may be notably hydrogen, an $NR_4$ group, or a $PR_4$ group with R selected from hydrogen or a hydrocarbon radical.

These catalysts may be obtained by any method known to those skilled in the art. Thus, the EP 657 386 and WO 95/17963 patents may be referred to for the preparation of iridium-based catalytic solutions which are appropriate for the implementation of the present invention.

It is to be noted that the reaction according to the invention may be carried out with a catalytic system which comprises, besides iridium, one or more other metals from Group VIII. More particularly, the reaction may be carried out with an association of rhodium and iridium, or even an association of ruthenium and iridium, or even a catalytic system based on these three metals.

If such a variant is adopted, the molar ratio of iridium and the other associated metals is more particularly between 1/10 and 10/1. Preferably, it is greater than 1/1.

As it has been mentioned previously, the isomerisation reaction according to the invention is carried out in the presence of water and a solvent.

As regards the solvent, this can comprise one or more carboxylic acids, as well as other compounds designated as co-solvents in the present invention.

More particularly, said solvent is selected from the carboxylic acids. According to a particular embodiment of the present invention, the carboxylic acid is selected from the aliphatic acids having from 2 to 10 carbon atoms, preferably from 2 to 5 carbon atoms. According to a particularly advantageous embodiment of the present invention, said carboxylic acid is acetic acid. The context of the present invention shall not be left in employing a mixture of the above-mentioned acids.

The reaction according to the invention is furthermore carried out in the presence of formic acid which is present in the medium, and consequently, counted amongst the carboxylic acids. Formic acid makes up an integral part of the solvents included in the reaction used.

The context of the present invention would not of course be left in using a additional solvent which is inert under the reaction conditions. As an example of this type of solvent, esters, ethers, ketones, amides, sulphoxides or even hydrocarbons may be cited. The preferred co-solvent is methyl acetate.

If co-solvents are employed, the amount of carboxylic acid is preferably greater than that of the co-solvent.

The method of the invention therefore consists in maintaining a specific partial carbon monoxide pressure and a specific methyl formate concentration during the reaction.

Thus, the partial carbon monoxide pressure is maintained between $0.1.10^5$ Pa and $25.10^5$ Pa.

The pressures are expressed in absolute Pascals, and have been measured in the hot, i.e. under the conditions of the temperature of the reaction.

According to a more particular implementation of the invention, a partial carbon monoxide pressure is maintained above $0.5.10^5$ Pa and preferably above $10^5$ Pa.

The partial carbon monoxide pressure is advantageously below $15.10^5$ Pa. More particularly, it is below $10.10^5$ Pa.

A second important characteristic of the present invention is that the methyl formate content is kept below 20% by weight of the reaction mixture.

Preferably, said above-mentioned ester content does not go over 10% by weight of the reaction mixture. According to a particularly advantageous embodiment of the present invention, the methyl formate content does not go over 5% by weight of the reaction mixture.

When the reaction is carried out continuously, the above-mentioned characteristics are preferably kept constant throughout the reaction. It is to be noted that the partial carbon monoxide pressure may move around during the reaction, insofar as it is always found within the above-mentioned range.

When the reaction is carried out discontinuously, the amount of methyl formate is kept lower than the values indicated although going down, since said ester is consumed by the reaction. As for the partial carbon monoxide pressure, it may or may not be kept constant, provided that it is found within the range of above-mentioned values.

Both the characteristics which have just been clarified are essential for obtaining a method whose productivity is considerably improved.

The isomerisation method according to the invention is carried out in the presence of water. More particularly, the amount of water, expressed by weight of the reaction mixture, ranges between 0 (excluded) and 5%. Advantageously, said content is between 0 (excluded) and 2% by weight.

It is to be noted that the water plays an important role in the method. In fact, it participates in keeping the catalyst in solution, particularly in the partial vaporisation (flash) zone of the mixture which shall be described later. It also enables limiting the side-reactions known for the methods carried out under anhydrous conditions.

Furthermore, the amount of halogenated promoter maintained during the reaction is more particularly between 0.1 and 20% by weight of the reaction mixture. Preferably, the halogenated promoter content is between 1 and 15% by weight of the reaction mixture.

It is to be noted that the amounts of promoter indicated above are given as an indication. In fact, the person skilled in the art has all the same to find the optimal compromise between a maximal efficiency of this compound on the one hand, which has a beneficial effect on the activity and the stability of the catalyst, and on the other hand, economical considerations linked to the cost brought about by the recycling of this compound in the method.

The rest up to 100% is constituted by the solvent of the reaction. More particularly, the latter comprises the acid produced, optionally the ester produced, and formic acid.

According to a particular variant of the invention, the amount of formic acid present in the reaction medium is kept below 15% by weight of the reaction mixture. Preferably, the formic acid content is kept below 12% and more particularly below 10% by weight of the reaction mixture.

Furthermore, according to an advantageous embodiment of the present invention, the amount of free carboxylic acids present in the reaction mixture is greater than 25% by weight of said mixture and such that the whole of the constituents of the reaction mixture represents 100% by weight of the reaction mixture. More particularly, the amount of free carboxylic acids is greater than 30% by weight of the reaction mixture, and preferably it is greater than 40% by weight of the reaction mixture.

In the case where the co-solvent is present, preferably methyl acetate, the weight content of it is preferably lower than or equal to that of the acetic acid.

It is to be noted that the formic acid/methyl acetate molar ratio may be different from 1 under the conditions of the reaction, i.e. greater than or less than this value. The reaction may obviously be carried out with a molar ratio equal to 1.

Generally, the total iridium concentration in the reaction medium is between 0.1 and 100 mmol/l, preferably between 1 and 25 mmol/l.

The isomerisation reaction, object of the present invention, is preferably carried out in the presence of a corrosive metals content of lower than 2,000 ppm. The corrosive metals are especially iron, nickel, chromium, molybdenum. The corrosive metals content in the reaction mixture is maintained by the methods known to the person skilled in the art, such as for example, selective precipitation, liquid liquid extraction, passing through ion exchange resins.

The reaction is generally carried out at a temperature between 150 and 250° C. More particularly, the reaction temperature is between 175 and 210° C. Preferably, it is between 175 and 200° C.

The total pressure under which the reaction is carried out is generally greater than atmospheric pressure. More particularly, it is lower than $100.10^5$ Pa and preferably lower than or equal to $50.10^5$ Pa. The pressures are expressed in absolute Pascals, and are measured in the hot, i.e. under the conditions of temperature of the reaction.

The reaction is carried out in apparatuses which are resistant to the corrosion created by the medium. Thus, zirconium or even alloys of the Hastelloy® C or B type are particularly convenient under the conditions of carrying out the reaction.

During the starting up of the reaction, the various components are introduced into an appropriate reactor, equipped with means of stirring in order to ensure a good homogeneity of the reaction mixture. It is to be noted that if the reactor comprises preferably a mechanical means of stirring the reaction mixture, it is not excluded to operate without such means, it being possible for the homogenisation of the mixture to be effected by the introduction of the carbon monoxide into the reactor.

It is to be noted that the reaction may be conveniently carried out in a reactor of the piston type.

The combination of several reactors of the stirring and piston types is of course envisagable.

The reaction mixture leaving the reactor is treated in an appropriate manner in order to separate the products of the reaction mixture which notably comprise the catalyst.

For this, and in the case of carrying out the reaction continuously, a conventional technique may be employed for example which consists in expanding the mixture in a way so as to cause a partial vaporisation of the latter. This operation can be carried out using a valve which enables expanding the mixture, the latter being then introduced into a separator (known as a flash separator). The operation may take place with or preferably without the contribution of heat, i.e. under adiabatic conditions.

According to a variant of the invention, the water content in the partial vaporisation zone is kept for the vaporised part at a value of at least 0.5% by weight with respect to the weight of this non-vaporised part. This can take place if need be by injection of water in said partial vaporisation zone i.e. in the flash separator.

The vaporised part which comprises the acetic acid and/or methyl acetate produced may be placed in contact and washed in the upper part of the flash separator by a liquid coming from purification installation downstream.

Upon leaving the flash separator, the non-vaporised part which notably comprises the catalyst which has remained in solution, totally or partially, is recycled advantageously to the reactor, conventionally by means of a pump.

The vaporised part which comprises the produced acetic acid and/or methyl acetate is then sent into a purification zone which comprises, usually, various distillation columns.

According to a variant of the invention, a supplementary placing in contact and washing may be carried out in the first distillation column with the aid of a liquid coming from the purification installations.

According to another variant of the invention, the reaction mixture, upon leaving the reactor, may be directly expanded in the first distillation column of the purification zone.

The various flows of separated material in the purification zone may be recycled towards the reactor or treated independently.

The acetic acid or methyl acetate obtained by this method is of sufficient quality to be sold without purification other than those known to the person skilled in the art and already in the public field.

The introduction of carbon monoxide may take place directly in the reactor, but also in the recycling zone of the non-vaporised liquid fraction, such that the carbon monoxide is not degasified directly towards the partial vaporisation zone of the reaction mixture. To this end, the introduction of carbon monoxide according to this latter possibility is more particularly carried out downstream from the reaction mixture recycling pump.

A concrete but non-limiting example of the invention is now going to be presented.

EXAMPLE

First of all, the catalytic solution is prepared as follows:
In an autoclave is introduced:
 105 g of iridium iodide,
 90 g of hydroiodic acid in 57% solution in water,
 910 g of acetic acid.

The autoclave is then pressurised to $50.10^5$ Pa (50 bar) of carbon monoxide.

The temperature is brought to 150° C.

The duration of the reaction is 4 hours.

The autoclave is then depressurised and then the reaction medium is cooled.

A red coloured solution is obtained which is decanted in order to obtain the catalytic solution.

The isomerisation reaction is carried out as follows:

In an autoclave in Hastelloy® B2, is introduced continuously a solution of iridium in acetic acid, prepared as above, acetic acid, methyl iodide, methyl formate and water.

The partial carbon monoxide pressure is kept constant at a value of $6.10^5$ Pa (6 bar).

The total pressure upon leaving the reactor is $25.10^5$ Pa (25 bar).

The temperature is kept at 190° C.±0.5° C.

The composition of the reaction mixture under steady state conditions is the following:

water: 0.20% methyl acetate: 7.8% methyl iodide: 12% formic acid: 3.7% methyl formate: 0.72% the iridium concentration is: 3,080 ppm acetic acid: made up to 100%

The composition of the reaction mixture, in weight percent, given with a precision in the order of 2%, is determined by measurement by vapour phase chromatography.

The calculation of the rate of isomerisation is carried out on the liquid resulting from the reactor, cooled to ambient temperature and, collected for a period of time between 30 and 60 minutes with respect to the flows of the compounds injected into the reactor during this same period, once the steady state conditions have been obtained.

A rate of isomerisation of 25 mol/h/l in acetic acid formed is obtained, the latter being in the form of acid and methyl acetate.

The proportion of these two products is the following: 75% of acetic acid and 25% of methyl acetate.

The only compounds detected during the analysis of the reaction mixture are methyl iodide, formic acid, methyl formate, methyl acetate, water and acetic acid.

We claim:

1. Method of preparing at least one compound selected from the group consisting of acetic acid and methyl acetate comprising isomerizing methyl formate in a reaction mixture comprising water, a solvent and a catalytic system comprising at least one halogenated promoter and at least one iridium-based compound, wherein carbon monoxide is present in the reaction mixture at a partial pressure between $0.1.10^5$ Pa and $25.10^5$Pa, methyl formate is maintained below 20% by weight of the reaction mixture and water is maintained in an amount which is at most 5% by weight of the reaction mixture.

2. Method of claim 1, wherein the partial carbon monoxide pressure is greater than or equal to $0.5.10^5$ Pa.

3. Method of claim 1, wherein the partial carbon monoxide pressure is lower than or equal to $15.10^5$ Pa.

4. Method of claim 1, wherein methyl formate is maintained below 10% by weight of the reaction mixture.

5. Method of claim 1, wherein the reaction mixture contains at most 2% by weight of water.

6. Method of claim 1, wherein the reaction mixture contains between 0.1 and 20% by weight of the halogenated promoter.

7. Method of claim 1, wherein the reaction mixture further contains a solvent which is selected from the group consisting of aliphatic carboxylic acids having 2 to 10 carbon atoms.

8. Method of claim 1, wherein the reaction mixture further contains formic acid in an amount maintained below 15% by weight.

9. Method of claim 8, wherein the formic acid is maintained below 10% by weight of the reaction mixture.

10. Method of claim 9, wherein the amount of said carboxylic acids free in the reaction mixture is greater than 25% by weight of said mixture.

11. Method of claim 1, wherein the reaction mixture further contains a co-solvent which is methyl acetate.

12. Method of claim 11, wherein the amount of the co-solvent by weight is lower than or equal to that of acetic acid.

13. Method of claim 1, wherein the halogenated promoter is selected from the group consisting of iodinated compounds and precursors of iodinated compounds.

14. Method of claim 1, wherein the reaction is carried out continuously.

15. Method of claim 1, wherein the partial pressure of carbon monoxide is less than or equal to $10.10^5$ Pa.

* * * * *

UNITED STATES PATENT AND TRADEMARK OFFICE
CERTIFICATE OF CORRECTION

PATENT NO. : 6,232,490 B1
DATED : May 15, 2001
INVENTOR(S) : Carl Patois et al.

It is certified that error appears in the above-identified patent and that said Letters Patent is hereby corrected as shown below:

Title page,
Item [57] ABSTRACT, in line 10, change "method" to -- methyl --.

Column 6,
Line 19, change "vaporized" to -- non-vaporized --.

Column 8,
Line 31, change "9" to -- 7 --.

Signed and Sealed this

Sixteenth Day of April, 2002

Attest:

Attesting Officer

JAMES E. ROGAN
*Director of the United States Patent and Trademark Office*